United States Patent

Liu et al.

[11] Patent Number: 6,037,771
[45] Date of Patent: Mar. 14, 2000

[54] SLIDING THIN-SLAB ACQUISITION OF THREE-DIMENSIONAL MRA DATA

[75] Inventors: Kecheng Liu; Brian K. Rutt, both of London, Canada

[73] Assignee: London Health Sciences Centre, London, Canada

[21] Appl. No.: 08/938,715

[22] Filed: Sep. 26, 1997

[30] Foreign Application Priority Data

Oct. 16, 1996 [CA] Canada ................................. 2187964

[51] Int. Cl.[7] ....................................................... G01V 3/00
[52] U.S. Cl. .............................................................. 324/309
[58] Field of Search ............................................... 324/309

[56] References Cited

U.S. PATENT DOCUMENTS

| | | | |
|---|---|---|---|
| 4,431,968 | 2/1984 | Edelstein et al. | 324/309 |
| 5,167,232 | 12/1992 | Parker et al. | 128/653.3 |
| 5,225,779 | 7/1993 | Parker et al. | 324/306 |
| 5,298,862 | 3/1994 | Hennig | 324/309 |

*Primary Examiner*—Christine K. Oda
*Assistant Examiner*—Tiffany A. Fetzner
*Attorney, Agent, or Firm*—Quarles & Brady, LLP

[57] ABSTRACT

A 3DFT gradient-recalled echo pulse sequence is employed to acquire NMR data from which an MR angiogram is produced. A thin slab excitation is employed and this thin slab is incremented in slice-thickness steps through the volume of interest as the NMR data is acquired. Navigator echoes are acquired at each thin slab location to correct the NMR data for phase errors produced by the sliding slab technique.

11 Claims, 5 Drawing Sheets

SLIDING THIN-SLAB ACQUISITION OF THREE-DIMENSIONAL MRA DATA

BACKGROUND OF THE INVENTION

The field of the invention is nuclear magnetic resonance imaging methods and systems. More particularly, the invention relates to the acquisition of three-dimensional data sets and the reconstruction of images from such data sets.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

The present invention will be described in detail with reference to a variant of the well known Fourier transform (FT) imaging technique, which is frequently referred to as "spin-warp". The spin-warp technique is discussed in an article entitled "Spin-Warp NMR Imaging and Applications to Human Whole-Body Imaging" by W. A. Edelstein et al., *Physics in Medicine and Biology*, Vol. 25, pp. 751–756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of views that are acquired during the scan to produce a set of NMR data from which an entire image can be reconstructed.

In a three-dimensional implementation of the spin-warp method phase encoding of the spin-echo signals is performed along two orthogonal axes. As described in U.S. Pat. No. 4,431,968 entitled "Method of Three-Dimensional NMR Imaging Using Selective Excitation," a thick slab of spins is excited by applying a slab-selection gradient ($G_z$) in the presence of a selective RF excitation pulse and then a first phase encoding gradient ($G_z$) along the same axis and a second phase encoding gradient ($G_y$) are applied before the NMR signal acquisition in the presence of a readout gradient ($G_x$). For each value of the $G_z$ phase encoding gradient, the $G_y$ phase encoding is stepped through all its values to sample a three-dimensional region of k-space. By selectively exciting a slab, NMR signals are acquired from a controlled 3-dimensional volume.

MR angiography (MRA) has been an active area of research. Two basic techniques have been proposed and evaluated. The first class, time-of-flight (TOF) techniques, consists of methods which use the motion of the blood relative to the surrounding tissue. The most common approach is to exploit the differences in signal saturation that exist between flowing blood and stationary tissue. This is known as flow-related enhancement, but this effect is misnamed because the improvement in blood-tissue contrast is actually due to the stationary tissues experiencing many excitation pulses and becoming saturated. Flowing blood, which is moving through the excited section, is continually refreshed by spins experiencing fewer excitation pulses and is, therefore, less saturated. The result is the desired image contrast between the high-signal blood and the low-signal stationary tissues.

MR methods have also been developed that encode motion into the phase of the acquired signal as disclosed in U.S. Pat. No. Re. 32,701. These form the second class of MRA techniques and are known as phase contrast (PC) methods. Currently, most PC MRA techniques acquire two images, with each image having a different sensitivity to the same velocity component. Angiographic images are then obtained by forming either the phase or complex difference between the pair of velocity-encoded images. Phase contrast MRA techniques have been extended so that they are sensitive to velocity components in all three orthogonal directions.

When 3D imaging methods are employed to produce an MRA image, the size of the excited slab becomes a limiting factor. To improve the diagnostic utility of the MRA image it is desirable to increase the slab thickness to increase the field of view along the slab-select axis. However, time-of-flight (TOF) MRA images decrease in quality as the slab thickness increases due to the saturation of the spins as they flow through the excited slab. That is, due to the increased thickness of the excited slab, blood remains in the slab for a longer time and becomes saturated by the selective RF excitation pulse. As a result, fresh blood entering the slab appears much brighter in the reconstructed image than blood which has remained in the slab for a number of excitations.

One solution to this problem is to acquire NMR data from the desired three-dimensional region by sequentially exciting a series of thin slabs and concatenating the NMR data acquired therefrom. As described in U.S. Pat. No. 5,167,232 entitled "Magnetic Resonance Angiography By Sequential Multiple Thin Slab Three Dimensional Acquisition," the thin slabs must be overlapped because slices on each slab boundary suffer from signal loss due to imperfect slab excitation profiles. As a result, a large percentage (e.g. up to 50%) of the acquired data is discarded because of the signal fall-off at the thin slab boundaries. Without this substantial thin slab overlap and consequent reduction in acquisition efficiency, a "venetian blind" or thin slab boundary artifact (SBA) is produced. This SBA artifact is characterized by a signal loss at slab boundaries, is flow dependent, and results in a signal intensity oscillation along blood vessels, which may result in a false depiction of vessel lumen diameter and over estimation of stenosis and atherosclerosis in clinical MRA images. On the other hand, discarding half of the acquired data is inefficient and significantly increases the scan time for a specified region of interest.

Another method for reducing the signal fall-off of flowing spins as they traverse the excitation slab is to use a ramped or "TONE" RF excitation pulse to compensate for progressive signal decay (see Purdy D., Cadena G., Laub G., The Design Of Variable Tip Angle Slab Selection (TONE) Pulses For Improved 3-D MR Angiography, Book of Abstracts: Society of Magnetic Resonance in Medicine, 1992, Berlin: Germany, p. 882). However, there are a number of inherent problems with this solution. Firstly, determination of the shape of the ramped RF pulses is empirical and inaccurate due to the unpredictable flow pattern of blood in vivo. Secondly, since the ramped RF pulses are only designed to compensate for flow in one direction, the use of such RF excitation pulses leads to an exaggeration of the slab boundary artifact when blood flow reverses its direction within the imaged volume. In other words, the ramped RF pulse technique increases sensitivity to flow direction. Finally, the use of ramped RF pulses can limit flexibility in the choice of flip angle, since the optimal flip angle and ramp angles are strongly correlated (i.e. fixing one constrains the other).

Yet another solution is to use frequency modulated (FM) RF pulses to perform quadratic phase encoding as disclosed in James G Pipe, Spatial Encoding and Reconstruction in MERI with Quadratic Phase Profiles, Magnetic Resonance Imaging 33:24-333, 1995. This method provides identical weighting to flow for every resolved element in the slice-selection direction and thus removes the slab boundary effect, thereby overcoming the problems inherent in the prior art techniques. However, the quadratic phase encoding technique suffers from three disadvantages. Firstly, it requires a specialized image reconstruction method which is not simple to implement on a conventional clinical MRI scanner. Secondly, due to the low-efficiency of quadratic phase RF pulses, the specific absorption rate (SAR) is higher than with conventional methods, which restrict its application to patients according to FDA guidelines on power deposition. Finally, the signal-to-noise ratio of angiograms performed with this method is dependent on flow direction due to on-resonance and off-resonance effects.

Another method for acquiring multiple highly-overlapping 2D slices is disclosed by Juergen Hennig in "Overlapping Section Coverage in Multisection Imaging," Journal of Magnetic Resonance Imaging, 1993, March/April, pages 425–432. This technique is claimed to solve the 'string-of-pearls' artifact in 2D time-of-flight MRA which is mainly caused by imperfect RF slice profiles. The key element of this method is a strategy for undersampling in the $k_y$-axis. In this method, the reconstruction of an image at any arbitrarily defined position along the slice selection direction is attempted using data sampled at discrete slice position locations. Thus, for example, on a designated image reconstruction plane, some $k_y$ lines will come from one acquired plane and some from another acquired plane. The disadvantage of this method is that artifacts such as blurring and other partial volume effects are seen. As the author of this method proposed, the best application of this technique is in producing a factor of two improvement in effective slice direction resolution. To accomplish this, however, there should be very little phase error across the slice so that phase conjugate symmetry can be used.

SUMMARY OF THE INVENTION

The present invention is a method for efficiently acquiring a three-dimensional NMR data set which minimizes the detrimental effects of saturated flowing spins and which does not produce slab boundary artifacts. More particularly, the present invention is a method for performing an NMR data acquisition in which a thin slab RF excitation is employed with a 3DFT pulse sequence, k-space is sampled completely along a through-slab axis (e.g. $k_z$) and a distributed sampling of a number of locations along an in-slab phase encoding axis (e.g. $k_y$) is made before the thin slab RF excitation is translated along the through-slab axis an increment of distance substantially smaller than the slab thickness. Sampling of k-space is repeated after each increment of thin slab translation, but the distributed sampling of locations along the in-slab phase encoding axis (e.g. $k_y$) is different at each thin slab position until all of k-space along the in-slab axis has been completely sampled. A three-dimensional region of interest is thus sampled using a thin slab excitation which slides through the region during the scan. No slab boundaries occur in the acquired NMR data set because the in-slab phase encoding axis is sampled in an interleaved manner at each thin slab position.

A general object of the invention is to acquire a three-dimensional NMR data set as a series of thin slab acquisitions without producing slab boundary artifacts (SBA). Rather than acquiring slightly overlapping thin slabs of NMR data and concatenating them to form the desired three-dimensional data set, the present invention acquires the entire data set using a thin slab excitation that "slides" along the first axis (e.g. z) as data is acquired along the other two axes (e.g. y and x). Because the phase encoding sampling $k_y$ is performed at many thin slab locations and this sampling is interleaved with the sampling at other thin slab locations, no slab boundary is present. As a result, no slab boundary artifacts are present in the reconstructed image.

Another object of the invention is to efficiently acquire a three-dimensional NMR data set. Very little overlapping or redundant data is acquired and discarded. Only a portion of the $k_y$ sampling is acquired at each thin slab location and the remainder of the $k_y$ sampling is performed at subsequent thin slab locations as the slab slides incrementally along the slice selection axis z.

Yet another object of the invention is to acquire a three-dimensional NMR data base for magnetic resonance angiography. By using thin slab excitation, flowing spins produce substantially the same signal intensity at all locations in the slab regardless of their velocity or direction. Flow artifacts are not produced at slab boundaries because no such boundaries are present when the incremental, sliding of the thin slab excitation is employed according to the present invention.

Another object of the invention is to correct for phase and amplitude errors in the acquired 3D NMR data set. Navigator NMR signals may be acquired at each thin slab location as it slides through the region of interest. Phase and amplitude corrections can be determined from the navigator signals and offsetting corrections made to the views acquired at the corresponding thin slab locations.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

GENERAL DESCRIPTION OF THE INVENTION

Figure 4:
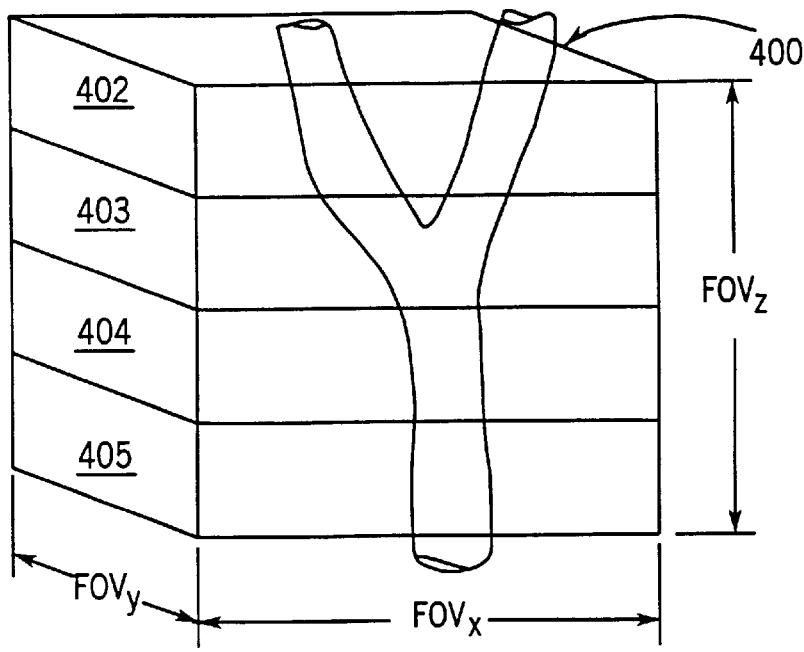
FIG. 4 is a schematic representation of a 3D region of interest to be imaged according to the present invention.

Referring particularly to FIG. 4, an angiogram is to be produced of a vessel (eg. carotid bifurcation) by acquiring a 3D NMR data set from which an image can be reconstructed. The 3D volume of interest is indicated at 400 and the present invention deals with how the NMR data is acquired so that the most clinically useful MRA can be produced.

Three-dimensional acquisitions employ pulse sequences that excite a slab of spins in the volume of interest. The thickness of this slab may encompass the entire volume of interest (eg. slab thickness=$FOV_z$), but when it becomes too thick, the signal from spins flowing through the slab become saturated and the intensity of the MRA image of a blood vessel drops at the "downstream" side of the slab. To alleviate this problem a thinner slab excitation may be used and a series of thin slab acquisitions may be performed to acquire data for the entire volume of interest. That is, the entire k-space defined by the thin slab excitation is sampled and then the location of the thin slab excitation is shifted to the next region. Such concatenated thin slab acquisitions are indicated by thin slab regions 402–405, which together fill the volume of interest 400. As indicated above, image artifacts are produced at the boundaries of these thin slab regions 402–405, and these artifacts substantially reduce the clinical use of the reconstructed image.

Figure 5:
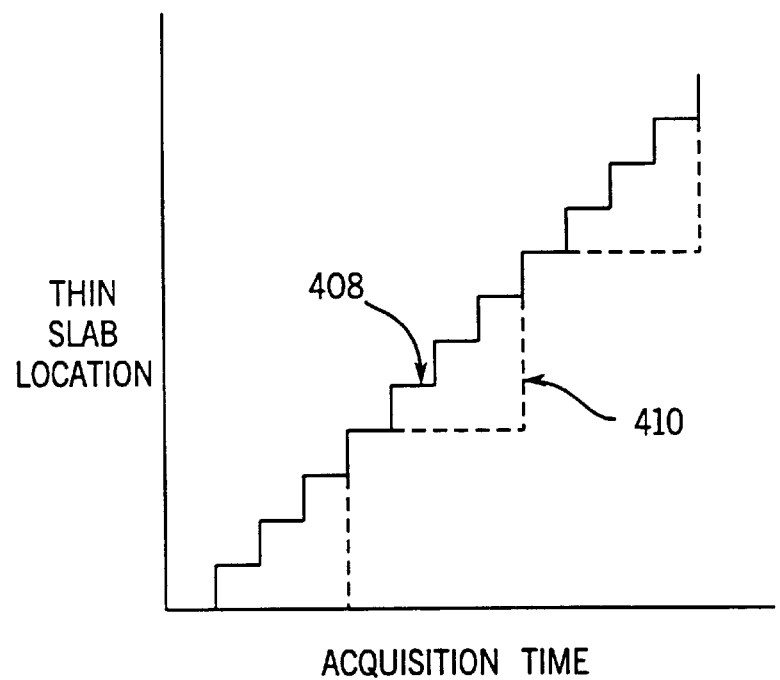
FIG. 5 is a graphic representation comparing the sliding translation of the thin slab excitation according to the present invention with a prior method.

The present invention employs a "sliding" thin slab acquisition of data from the volume of interest. At each thin slab location a portion of k-space is sampled and then the slab is moved a small distance (eg. one slice thickness) and another portion of k-space is sampled. The process continues and k-space is sampled such that when the thin slab has moved a distance equal to its thickness, all of k-space has been sampled. The process repeats for as many thin slab distances as required to sample the entire volume of interest. This sliding movement of the thin slab excitation is shown by line 408 in FIG. 5 where it can be compared with the prior art concatenation method indicated by dotted line 410.

Figure 6:
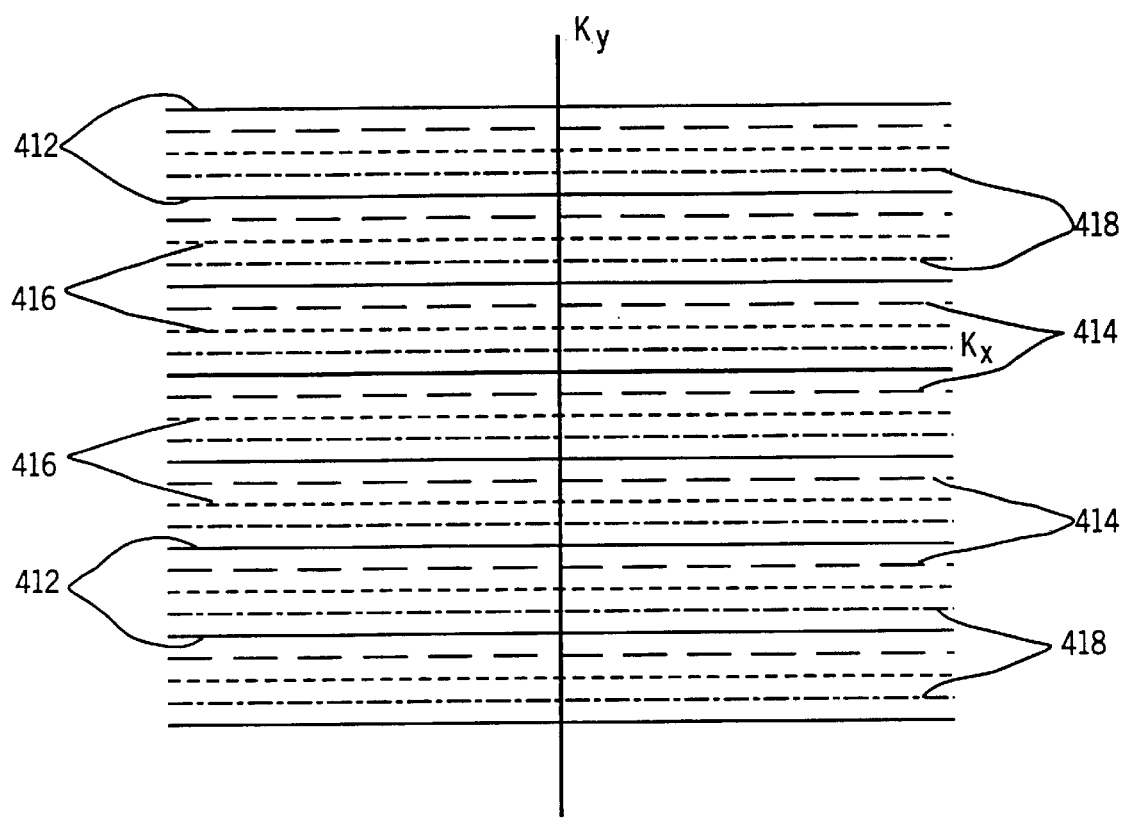
FIG. 6 is a graphic representation of the interleaved sampling of k-space practiced by the preferred embodiment of the invention.

To reduce image artifacts caused by signal variations along the slab-select axis, k-space is sampled in an interleaved manner. As shown in FIG. 6, for example, at the first thin slab location all of $k_x$ space and all of $k_z$ space (not shown in FIG. 6) are sampled, but the $k_y$ axis is partially sampled at locations indicated by solid lines 412, which are distributed along the entire extent of the $k_y$ axis. After the thin slab slides one increment along the slab-select axis, $k_z$ and $k_x$ are completely sampled again, but at different locations distributed along the $k_y$ phase encoding axis indicted by dotted lines 414. These sample locations are spread along the $k_y$ axis and they interleave with the previous sample locations 412. The thin slab may be moved again and further interleaved samples acquired along the $k_y$ axis as indicated by lines 416 and 418 until all of k-space has been sampled. The sequence may then be repeated if necessary to acquire data over another thin slab.

As a result of the sliding slab and interleaved sampling of k-space, the variations in signal strength along the slab-select axis and the resulting boundary image artifacts are eliminated. The variations in signal along the slab-select axis are in effect distributed evenly along the slab-select axis by the sliding and interleaved acquisition strategy.

However, this benefit does not come without a price—the variations produce an equivalent modulation of the amplitude of the signal in the phase encoding direction ($k_y$). In addition, the sliding thin slab imparts a fixed phase shift to the interleaved data acquired at successive incremental locations. A further aspect of the present invention is the manner in which the acquired three-dimensional data set is processed to offset the amplitude variations and fixed phase shifts produced by the sliding thin slab method and to reduce the image artifacts produced by signal modulation along the phase encoding axis.

The method of the present invention produces a periodic amplitude modulation in the $k_y$ phase encoding direction due to the transfer of signal variations in the slab profile from the slab-select axis to the $k_y$ phase encoding axis. The period of this amplitude modulation is typically equal to the number of incremental sliding movements per slab, while the number of full periods is equal to the number of $k_y$ lines divided by the number of increments. This amplitude modulation function along the phase encoding direction causes a ghosting artifact along the phase encoding direction in the image. The amplitude of the ghosts depends on the degree of modulation and hence on the smoothness of the velocity-dependent amplitude modulation function. In practice, it has been observed that the peak-to-peak amplitude modulation along the phase encoding axis almost never exceeds 50%, resulting in a primary ghost artifact with less than 10% of the original object intensity. If this periodic amplitude fluctuation is demodulated by using, for example, a navigator echo signal collection (and/or a moving average demodulation technique) the ghost artifact intensity can easily be suppressed by a factor of 1.3–2.0 or more. In addition, ghost artifact intensity in the final angiogram is further suppressed by application of the maximum-intensity-projection (MIP) algorithm.

The data acquired according to the present invention is acquired in an interleaved fashion along $k_y$ at each incremental position of the thin slab, resulting in multiple data segments along the $k_y$ axis. Because the slab is sliding, the phase of the data in each segment may not be consistent across segment boundaries, due to such factors as non-ideal system performance, RF phase error, and time-varying flow of spins. Such phase inconsistencies should be removed to avoid corruption of the reconstructed images with ghost artifacts similar to those produced by amplitude modulation.

To correct these phase jumps between data segments along the phase encoding axis, a navigator echo can be acquired and used to correct the phase. The static slice-position-dependent phase error can be easily estimated from the acquired navigator echo data and subtracted from the data in the corresponding k-space segment. Eliminating the flow-induced phase is more complicated, but this phase error can be minimized by: i) carefully designing the acquisition order such that the navigator echo is acquired so that it closely estimates the flow induced phase at the center of $k_y$, and ii) utilizing a short echo time to minimize flow induced phase shifts. By using these two strategies, flow-induced phase errors are largely removed.

The correction of the acquired data is accomplished as follows. First, for phase encoding views $k_y$ belonging to the ith interleaf (incremental slab position), we assume that the acquired signals are modulated by constant amplitude and phase factors, $A_i$ and $\phi_i$, respectively. The data following a Fourier transformation along the readout axis x can thus be written as:

$$\tilde{s}_i(x,k_y) = s_i(x,k_y) \cdot [A_i e^{j\phi_i}] \text{ with } i=1, \ldots, N_{Int} \quad (1)$$

where $s_i(x, k_y)$ is the unmodulated signal, and $N_{Int}$ is the total number of interleaves. $N_{Int}$ is usually chosen so that it is equal to $N_z$, the number of unblanked slices per slab along the z-axis, in order to achieve the maximum suppression of the slab boundary artifact. The number of $k_y$ phase encoding views in each interleaf is thus determined by $N_y/N_{Int}$, where $N_y$ is the total number of phase encoding views to be collected. To remove $\phi_i$, and/or $A_i$, the following correction is performed:

$$\hat{s}_i(x,k_y) \approx \tilde{s}_i(x,k_y) \cdot [\hat{A}_i^{-1} e^{-j\hat{\phi}_i}] = s_i(x,k_y) \cdot [A_i e^{j\phi_i}][\hat{A}_i^{-1} e^{-j\hat{\phi}_i}] \quad (2)$$

where $\hat{\phi}_i$ and $\hat{A}_i$ are obtained, for example, by analyzing the navigator echo signal acquired during the ith interleaf. There are several ways to estimate $\hat{\phi}_i$ and $\hat{A}_i$. One method is to obtain $\hat{A}_i$ as the signal amplitude at the navigator signal echo peak, and $\hat{\phi}_i$ as the phase at the echo peak of the navigator signal (or averaged in the vicinity of this peak). The navigator echoes are obtained with the Y-phase encoding gradient switched off ($G_y$=0). After performing a Fourier transformation of these echoes along the $k_z$ slab-select axis, the estimation of $\hat{A}_i$ and $\hat{\phi}_i$ is then performed at the peak of the navigator signals in ($k_x$, $k_y$, z) space. If a Fourier transformation is performed along both the readout axis (x) and the slab-select axis (z) prior to the estimation, one dimensionally resolved $\hat{A}_i(X)$ and $\hat{\phi}_i(X)$ can be acquired, allowing the possibility of an even more accurate correction.

In the ideal case, when the estimated phase and amplitude errors are equal to the actual errors:

$$\phi_i = \hat{\phi}_i; \text{ and}$$

$$A_i = \hat{A}_i$$

the unmodulated signal $s_i(x,k_y)$ will be perfectly restored. Amplitude demodulation as described above must be performed with care, however, since the signal-to-noise ratio can be seriously degraded if the estimated error amplitude $\hat{A}_i$ approaches zero.

DESCRIPTION OF THE PREFERRED EMBODIMENT

Figure 1:
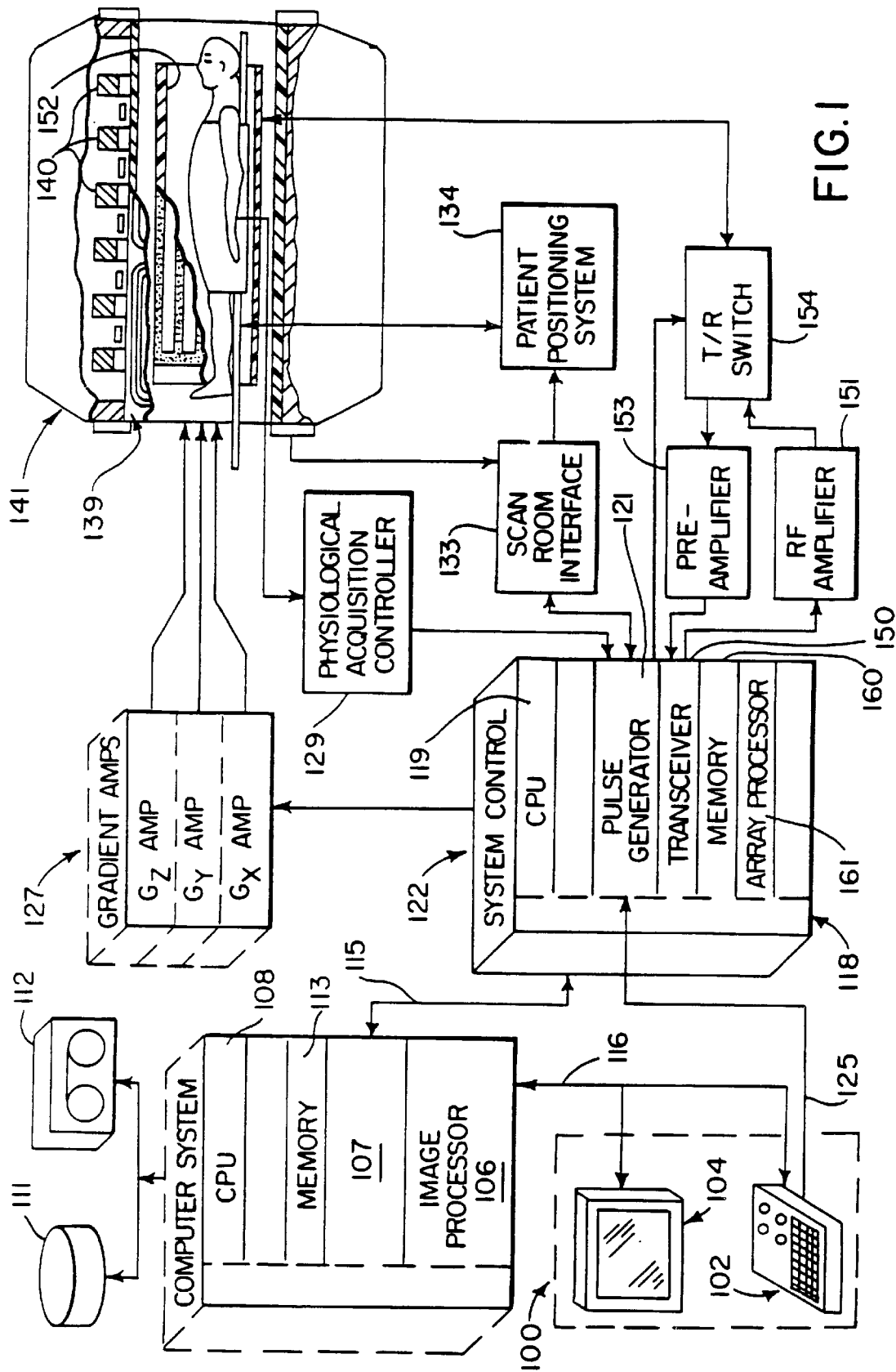
FIG. 1 is a block diagram of a known MRI system which has been modified to employ the present invention.

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 102 where it is stored in the disk memory 111. In response to commands received from the operator console 100, this image data may be archived on the tape drive 112, or it may be further processed by the image processor 106 and conveyed to the operator console 100 and presented on the display 104.

Figure 2:
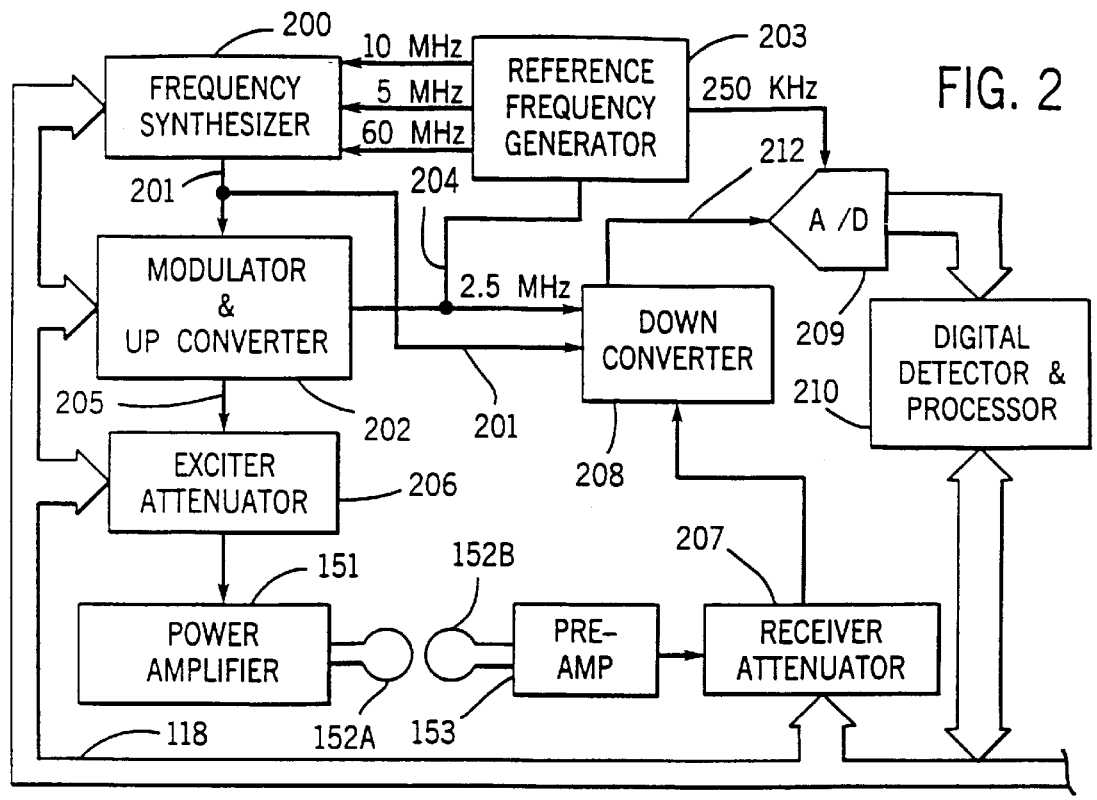
FIG. 2 is an electrical block diagram of the transceiver which forms part of the MRI system of FIG. 1.

Referring particularly to FIGS. 1 and 2, the transceiver 150 produces the RF excitation field B1 through power amplifier 151 at a coil 152A and receives the resulting signal induced in a coil 152B. As indicated above, the coils 152A and B may be separate as shown in FIG. 2, or they may be a single wholebody coil as shown in FIG. 1. The base, or carrier, frequency of the RF excitation field is produced under control of a frequency synthesizer 200 which receives a set of digital signals from the CPU module 119 and pulse generator module 121. These digital signals indicate the frequency and phase of the RF carrier signal produced at an output 201. The commanded RF carrier is applied to a modulator and up converter 202 where its amplitude is modulated in response to a signal R(t) also received from the pulse generator module 121. The signal R(t) defines the envelope of the RF excitation pulse to be produced and is produced in the module 121 by sequentially reading out a series of stored digital values. These stored digital values may, in turn, be changed from the operator console 100 to enable any desired RF pulse envelope to be produced.

The magnitude of the RF excitation pulse produced at output 205 is attenuated by an exciter attenuator circuit 206 which receives a digital command from the backplane 118. The attenuated RF excitation pulses are applied to the power amplifier 151 that drives the RF coil 152A. For a more detailed description of this portion of the transceiver 122, reference is made to U.S. Pat. No. 4,952,877 which is incorporated herein by reference.

Referring still to FIGS. 1 and 2 the signal produced by the subject is picked up by the receiver coil 152B and applied through the preamplifier 153 to the input of a receiver attenuator 207. The receiver attenuator 207 further amplifies the signal by an amount determined by a digital attenuation signal received from the backplane 118.

The received signal is at or around the Larmor frequency, and this high frequency signal is down converted in a two step process by a down converter 208 which first mixes the NMR signal with the carrier signal on line 201 and then mixes the resulting difference signal with the 2.5 MHz reference signal on line 204. The down converted NMR signal is applied to the input of an analog-to-digital (A/D) converter 209 which samples and digitizes the analog signal and applies it to a digital detector and signal processor 210 which produces 16-bit in-phase (I) values and 16-bit quadrature (Q) values corresponding to the received signal. The resulting stream of digitized I and Q values of the received signal are output through backplane 118 to the memory module 160 where they are employed to reconstruct an image.

The 2.5 MHz reference signal as well as the 250 kHz sampling signal and the 5, 10 and 60 MHz reference signals are produced by a reference frequency generator 203 from a common 20 MHz master clock signal. For a more detailed description of the receiver, reference is made to U.S. Pat. No. 4,992,736 which is incorporated herein by reference.

Figure 3:
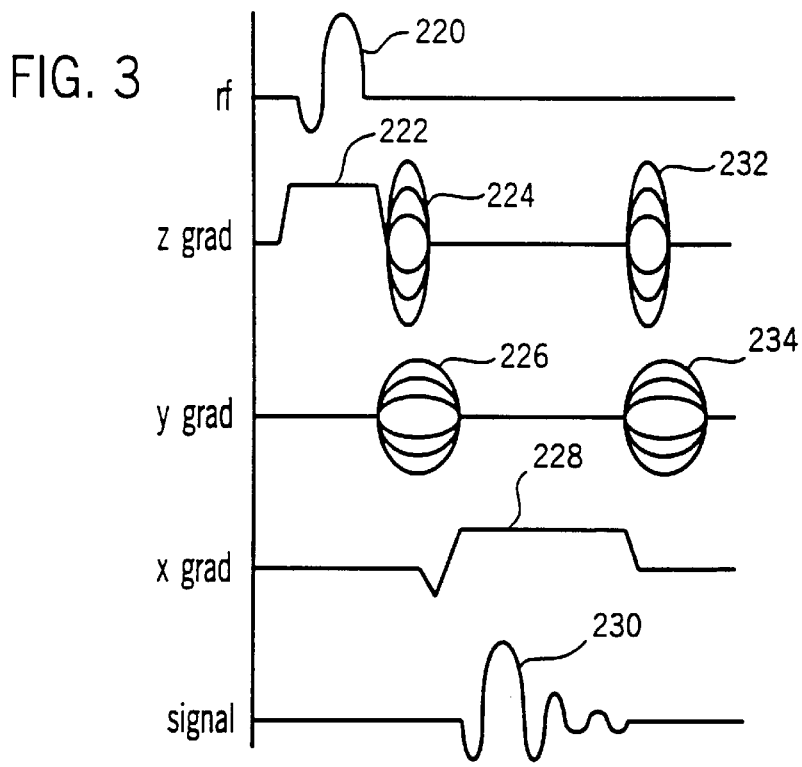
FIG. 3 is a graphic representation of the pulse sequence employed in the MRI system of FIG. 1 to practice the preferred embodiment of the invention.

Although the present invention can be used with a number of different pulse sequences, the preferred embodiment of the invention employs a 3D gradient recalled echo pulse sequence depicted in FIG. 3. The pulse sequence "3dtof" available on the General Electric 1.5 Tesla MR scanner sold under the trademark "SIGNA" with revision level 5.4 system software was used. It was modified to collect data in the k-space sampling patterns taught by the present invention.

Referring particularly to FIG. 3, an RF excitation pulse 220 having a flip angle of 25° and a bandwidth of +/−15.6 kHz is produced in the presence of a slab-select gradient pulse 222 to produce transverse magnetization in a 3D slab having a thickness of 16 mm as taught in U.S. Pat. No. 4,431,968. This is followed by a phase encoding gradient pulse 224 directed along the y axis. A readout pulse 228 directed along the x axis follows and a partial echo (60%) NMR signal 230 is acquired and digitized as described above. After the acquisition, rewinder gradient pulses 232 and 234 rephase the magnetization before the pulse sequence is repeated as taught in U.S. Pat. No. 4,665,365.

As is well known in the art, the pulse sequence is repeated and the phase encoding pulses 224 and 226 are stepped through a series of values to sample the 3D k-space. In the preferred embodiment 16 phase encodings are employed along the z axis and 144 phase encodings are employed along the y axis. For each particular y phase encoding, therefore, 16 acquisitions with 16 different z phase encodings are performed to sample completely along the $k_z$ axis. This is repeated 144 times with 144 different y phase encodings to sample completely along the $k_y$ axis. As will become apparent from the discussion below, the order in which this k-space sampling is performed is an important aspect of the present invention.

Sampling along the $k_x$ axis is performed by sampling the echo signal 230 in the presence of the readout gradient pulse 228 during each pulse sequence. It will be understood by those skilled in the art that only a partial sampling along the $k_x$ axis is performed and the missing data is computed using a homodyne reconstruction or by zero filling. This enables the echo time (TE) of the pulse sequence to be shortened to 3.0 msecs. and the pulse repetition rate (TR) to be shortened to 35 msecs or less.

To practice the present invention, the entire 3D k-space ($N_x$=256, $N_y$=144, $N_z$=16) defined by the excited slab is not sampled while the slab is fixed in one position. Instead, a repetitive sequence in which an "interleaf" is sampled, and the excited slab is moved one increment of distance is performed. In the preferred embodiment twelve separate interleafs are acquired and twelve incremental movements are made. Each increment of movement is equal to one slice thickness of approximately 1 mm. As a result, 144/12=12 separate $k_y$ phase encodings are acquired during each interleaf, along with one set of navigator signals. The k-space sampling strategy for three of the acquired interleafs is shown in Table 1.

TABLE 1

| | | |
|---|---|---|
| Interleaf 1: | ky = −72, | kz=(−8, . . . , 7) |
| | ky = −60, | kz=(−8, . . . , 7) |
| | ky = −48, | kz=(−8, . . . , 7) |
| | ky = −36, | kz=(−8, . . . , 7) |
| | ky = −24, | kz=(−8, . . . , 7) |
| | ky = −12, | kz=(−8, . . . , 7) |
| | NAVIGATOR SIGNALS | |
| | ky = 0, | kz=(−8, . . . , 7) |
| | ky = 12, | kz=(−8, . . . , 7) |
| | ky = 24, | kz=(−8, . . . , 7) |
| | ky = 36, | kz=(−8, . . . , 7) |
| | ky = 48, | kz=(−8, . . . , 7) |
| | ky = 60, | kz=(−8, . . . , 7) |
| Interleaf 2: | ky = −71, | kz=(−8, . . . , 7) |
| | ky = −59, | kz=(−8, . . . , 7) |
| | ky = −47, | kz=(−8, . . . , 7) |
| | ky = −35, | kz=(−8, . . . , 7) |
| | ky = −23, | kz=(−8, . . . , 7) |
| | ky = −11, | kz=(−8, . . . , 7) |
| | NAVIGATOR SIGNALS | |
| | ky = 1, | kz=(−8, . . . , 7) |
| | ky = 13, | kz=(−8, . . . , 7) |
| | ky = 25, | kz=(−8, . . . , 7) |
| | ky = 37, | kz=(−8, . . . , 7) |
| | ky = 49, | kz=(−8, . . . , 7) |
| | ky = 61, | kz=(−8, . . . , 7) |
| Interleaf 12: | ky = −61, | kz=(−8, . . . , 7) |
| | ky = −49, | kz=(−8, . . . , 7) |
| | ky = −37, | kz=(−8, . . . , 7) |
| | ky = −25, | kz=(−8, . . . , 7) |
| | ky = −13, | kz=(−8, . . . , 7) |
| | NAVIGATOR SIGNALS | |

TABLE 1-continued

| | |
|---|---|
| ky = −1, | kz=(−8, . . . , 7) |
| ky = 11, | kz=(−8, . . . , 7) |
| ky = 23, | kz=(−8, . . . , 7) |
| ky = 35, | kz=(−8, . . . , 7) |
| ky = 47, | kz=(−8, . . . , 7) |
| ky = 59, | kz=(−8, . . . , 7) |
| ky = 71, | kz=(−8, . . . , 7) |

At each $k_y$ phase encoding all 16 $k_z$ phase encodings are acquired. However, only 12 $k_y$ phase encodings are acquired during each interleaf, and these are spaced apart, or distributed, to sample substantially uniformly throughout the full extent of $k_y$-space. At the completion of 12 interleafs all 144 views, or $k_y$ phase encodings, have been acquired. The slab is moved one increment and the cycle is repeated as many times as necessary to increment the excited slab along the z-axis the entire extent of the 3D volume of interest.

Because the excited slab is incremented after each interleaf, when all $k_y$ phase encodings are collected together to form a complete 3D k-space data set, phase errors and phase offsets are present. To remove these, navigator signals are also acquired during each interleaf (i.e. slab location). As indicated in Table 1, the navigator signals are acquired near the center of each interleaf acquisition at the time when the center of k-space is being acquired. This insures that the central views which dominate the reconstructed image are more accurately corrected using the navigator signal information.

Sixteen navigator signals are acquired during each interleaf. The same pulse sequence shown in FIG. 3 and described above is used, but the $k_y$ phase encoding is set to zero. The $k_y$ phase encoding is stepped through its sixteen values to produce a corresponding set of sixteen navigator signals. These sixteen navigator signals are digitized and used in correcting the phase of the views acquired during the same interleaf.

In the preferred k-space sampling pattern described above the $k_y$ sampling is interleaved and the order in which the thin slab is translated through the region of interest is sequential. An alternative method of sampling k-space according to the present invention is to sample $k_y$ in sequence and interleave the translation of the thin slab. In the following tables which illustrate the preferred "sliding interleaf" method and the alternative "skipping interleaf" method we assume: the number of $k_z$-encodings ($N_z$) is 16 (−8..7), the number of $k_y$-encodings ($N_y$) is 16 (−8..7), the total number of interleafs, or interleaf locations ($N_{int}$) is 4, and the number of $k_y$ samples per interleaf is therefore 4 ($N_y/N_{int}$) The repetition time of the pulse sequence is TR, the time to acquire the 16 $k_z$-samples in the $k_z$ inner loop is $T_R(z)=N_z \times TR$.

Table 2 illustrates the sliding interleaf method in which the interleaf location slides sequentially through the four thin slab locations during the sampling of k-space.

TABLE 2

| Time scale | Interleaf location | Slab position offset | $k_y$ | $k_z$ | Slab Status after acquisition |
|---|---|---|---|---|---|
| $T_R$ (Z) | 1 | 0 | −8 | −8 . . 7 | static |
| $2T_R$ (Z) | 1 | 0 | −4 | −8 . . 7 | static |
| $3T_R$ (Z) | 1 | 0 | 0 | −8 . . 7 | static |
| $4T_R$ (Z) | 1 | 0 | 4 | −8 . . 7 | Sliding |
| $5T_R$ (Z) | 2 | THK | −7 | −8 . . 7 | static |

TABLE 2-continued

| Time scale | Interleaf location | Slab position offset | $k_y$ | $k_z$ | Slab Status after acquisition |
|---|---|---|---|---|---|
| $6T_R$ (Z) | 2 | THK | −3 | −8 . . 7 | static |
| $7T_R$ (Z) | 2 | THK | 1 | −8 . . 7 | static |
| $8T_R$ (Z) | 2 | THK | 5 | −8 . . 7 | Sliding |
| $9T_R$ (Z) | 3 | 2xTHK | −6 | −8 . . 7 | static |
| $10T_R$ (Z) | 3 | 2XTHK | −2 | −8 . . 7 | static |
| $11T_R$ (Z) | 3 | 2xTHK | 2 | −8 . . 7 | static |
| $12T_R$ (Z) | 3 | 2XTHK | 6 | −8 . . 7 | Sliding |
| $13T_R$ (Z) | 4 | 3xTHK | −5 | −8 . . 7 | static |
| $14T_R$ (Z) | 4 | 3xTHK | −1 | −8 . . 7 | static |
| $15T_R$ (Z) | 4 | 3xTHK | 3 | −8 . . 7 | static |
| $16T_R$ (Z) | 4 | 3xTHK | 7 | −8 . . 7 | Sliding |

Table 3 illustrates the skipping interleaf method in which sampling along $k_y$ is performed in sequential order. Note that the thin slab location is incremented through the four interleaf locations and then jumps back to the first interleaf location four times during the sampling of k-space.

TABLE 3

| Time scale | Interleaf location | Slab position offset | $k_y$ | $k_z$ | Slab Status after acquisition |
|---|---|---|---|---|---|
| $T_R$ (Z) | 1 | 0 | −8 | −8 . . 7 | sliding |
| $2T_R$ (Z) | 2 | THK | −7 | −8 . . 7 | sliding |
| $3T_R$ (Z) | 3 | 2xTHK | −6 | −8 . . 7 | sliding |
| $4T_R$ (Z) | 4 | 3xTHK | −5 | −8 . . 7 | Jump back |
| $5T_R$ (Z) | 1 | 0 | −4 | −8 . . 7 | sliding |
| $6T_R$ (Z) | 2 | THK | −3 | −8 . . 7 | sliding |
| $7T_R$ (Z) | 3 | 2xTHK | −2 | −8 . . 7 | sliding |
| $8T_R$ (Z) | 4 | 3xTHK | −1 | −8 . . 7 | Jump back |
| $9T_R$ (Z) | 1 | 0 | 0 | −8 . . 7 | sliding |
| $10T_R$ (Z) | 2 | THK | 1 | −8 . . 7 | sliding |
| $11T_R$ (Z) | 3 | 2xTHK | 2 | −8 . . 7 | sliding |
| $12T_R$ (Z) | 4 | 3xTHK | 3 | −8 . . 7 | Jump back |
| $13T_R$ (Z) | 1 | 0 | 4 | −8 . . 7 | sliding |
| $14T_R$ (Z) | 2 | THK | 5 | −8 . . 7 | sliding |
| $15T_R$ (Z) | 3 | 2xTHK | 6 | −8 . . 7 | sliding |
| $16T_R$ (Z) | 4 | 3xTHK | 7 | −8 . . 7 | Jump back |

It should be apparent that many variations are possible in the above-described data acquisition procedure. Other pulse sequences may be employed and the particular parameters used in the pulse sequence can be varied considerably. Also, instead of moving the excitation slab incrementally during the scan, in the preferred embodiment the excitation slab can remain stationary and the patient can be moved sequentially through the region of interest. The optimal number of interleaves is the number of unblanked slices per slab. This will maximally suppress the slab boundary artifact. A smaller number of interleaves will be partially effective in suppressing the slab artifact. The smaller the number of interleaves, the poorer the suppression but the better the scan time efficiency and the ghosting artifact levels."

As indicated above, navigator signals may be acquired during the scan and information is extracted from each acquired navigator signal and this information is used to correct the phase and amplitude of each $k_y$ line, or view, acquired during the same interleaf and at the same $k_z$. In the preferred acquisition illustrated in Table 1, for example, each navigator signal corrects the 12 $k_y$ views.

The acquired navigator signals are first Fourier transformed along the z-axis. The location of the peak in the resulting transformed navigator signal is then determined using well known methods such as the maximum search method. The phase $\hat{\phi}_i$ of the transformed navigator signal at its peak (or an average of surrounding values) is then calculated from the arctangent of the ration of the complex signal values I and Q. The objective is to correct all the acquired image data to a single phase which in the preferred embodiment is selected as zero. Therefore, the correction is made by shifting the phase of the corresponding $k_y$ views by an amount $-\hat{\phi}_i$.

The amplitude correction is made by first determining the amplitude $\hat{A}_i$ of the transformed navigator signal at its detected peak. The amplitude is calculated by computing the square root of the sum of the squares of the complex signal values I and Q. The correction is made to the corresponding $k_y$ views by dividing their magnitudes by the correction amplitude $\hat{A}_i$.

Figure 7:
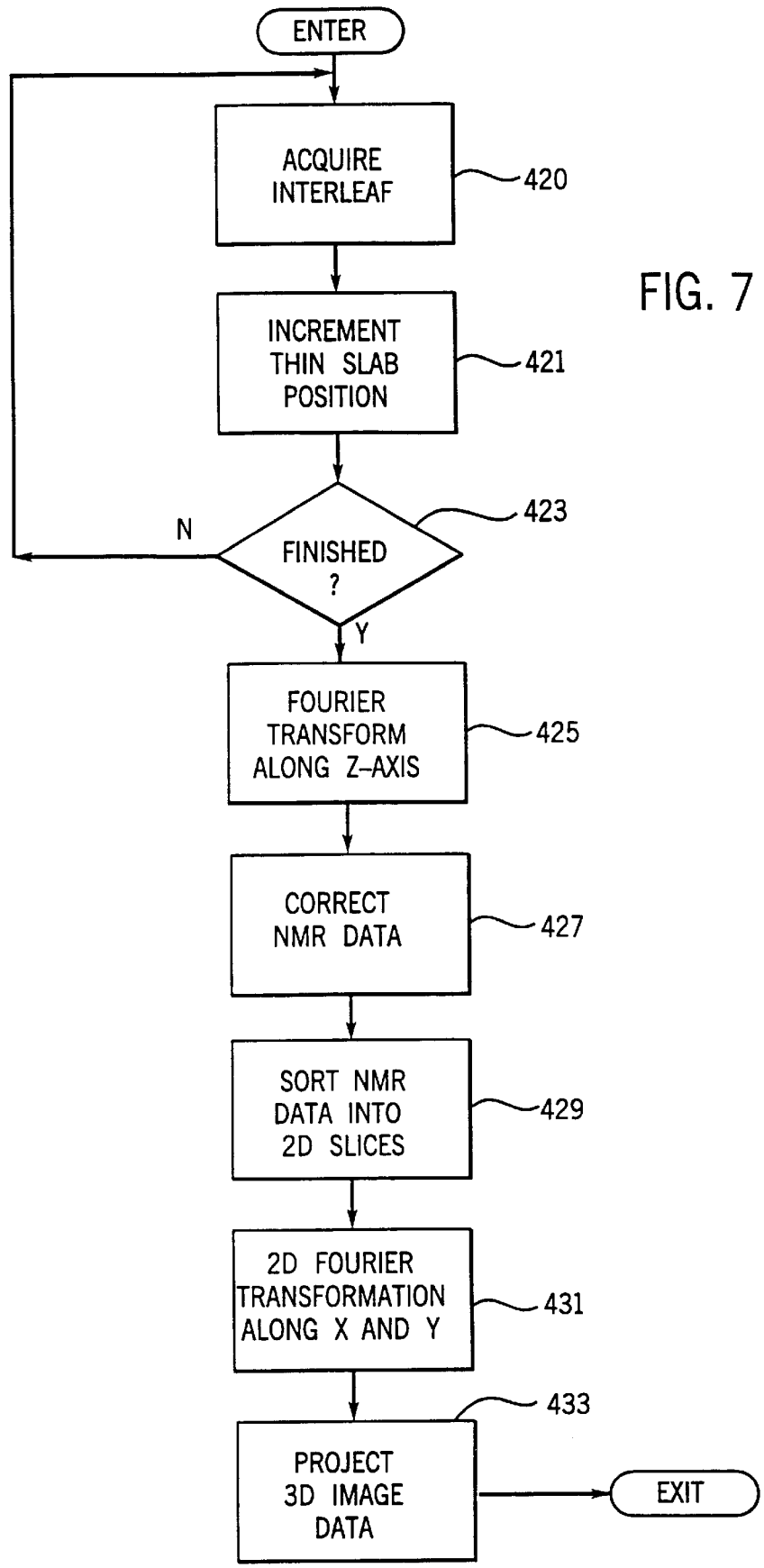
FIG. 7 is a flow chart which illustrates the steps performed by the MRI system of FIG. 1 to practice the preferred embodiment of the invention.

The present invention is practiced in the MRI system of FIG. 1 under the direction of a program which acquires the NMR signals, corrects them for phase and amplitude errors and reconstructs an MRA image. The steps performed are illustrated in FIG. 7, where process blocks 420 and 421 acquire the NMR data from the 3D region of interest using the above-described sliding interleaf method.

When the data acquisition is complete, as determined at decision block 423, a Fourier transformation of the entire data set is performed along the slab-select, z-axis as indicated at process block 425 using the array processor 161. If the NMR data is to be corrected, the navigator signals are also Fourier transformed along the z-axis and information is extracted from them and used to correct the NMR image data as indicated at process block 427.

As indicated at process block 429, the corrected NMR data set is sorted to re-order the $k_y$ lines, or views, into sequential order. This is merely the movement of data to form a 3D data set comprised of a set of 2D slices. As indicated at process block 431, a two-dimensional Fourier transformation along the x and y axes is then performed to produce a 3D image.

An MRA image is produced from the 3D image by projecting the data onto a 2D plane as indicated by process block 433. The most used technique for doing this is to project a ray from each pixel in the 2D plane through the 3D array of image data points and select the data point which has the maximum value. The value selected for each ray is used to control the brightness of its corresponding pixel in the 2D image. This method, referred to as the "maximum pixel technique," is very easy to implement and it gives aesthetically pleasing images. It is presently the preferred method. As is known in the art, a contrast agent may also be used and a 3D image without contrast may be used as a mask which is subtracted from the 3D image with contrast prior to projection onto a 2D image plane.

There are a number of variations possible in the processing of the acquired NMR data. A Fourier transformation may be performed along both the x and z axes before the corrections and sorting steps are performed. More accurate corrections can be made to reflect differences in flow conditions along the x-axis, but when this method is used more computation is required. Also, the correction step may not be required to obtain clinically useful images in some applications, or the correction of phase only may be required in other applications.

We claim:

1. A method for producing an image with NMR data acquired from a three-dimensional volume of interest, the steps comprising:
   a) producing a slab-selective RF excitation pulse which produces transverse magnetization in a thin slab located within said three-dimensional volume of interest;
   b) producing a first phase encoding gradient pulse which samples k-space along a first axis passing through the thin slab;
   c) producing a second phase encoding gradient pulse which samples k-space along a second axis oriented in the plane of the thin slab;
   d) acquiring an NMR signal in the presence of a readout gradient which samples k-space along a third axis oriented in the plane of the thin slab and perpendicular to the second axis;
   e) repeating steps a) through d) a plurality of times and changing the first phase encoding gradient pulse to sample k-space completely along said first axis;
   f) repeating step e) a plurality of times and changing the second phase encoding gradient pulse to sample k-space completely along said second axis;
   g) incrementing the position of the thin slab in the three-dimensional volume of interest along said first axis a plurality of times during the performance of step f) to sample k-space along said second axis at a corresponding plurality of thin slab locations; and
   h) reconstructing the image from the acquired NMR signals.

2. The method as recited in claim 1 in which steps f) and g) are performed a plurality of times to increment the position of the thin slab completely through said three-dimensional volume of interest along said first axis.

3. The method as recited in claim 1 in which the position of the thin slab is incremented by altering the RF excitation pulse produced in step a).

4. The method as recited in claim 1 in which the samples of k-space acquired in step f) along said second axis are interleaved with other of the samples of k-space acquired in step f) along said second axis when the thin slab position is incremented to a different position along said first axis.

5. The method as recited in claim 1 in which a gradient pulse is produced concurrently with the RF excitation pulse in step a) and cooperates therewith to locate said thin slab.

6. The method as recited in claim 1 in which a navigator pulse sequence is performed at each location of the thin slab as it is incremented along said first axis to acquire said NMR signals, and a navigator NMR signal is acquired at each thin slab location and employed to correct the corresponding NMR signals acquired at that thin slab location.

7. The method as recited in claim 6 in which the correction to the NMR signal changes the phase of the NMR signals.

8. A method for producing an image with NMR data acquired from a three-dimensional volume of interest, the steps comprising:
   a) producing a slab-selective RF excitation pulse which produces transverse magnetization in a thin slab located within said three-dimensional volume of interest;
   b) producing a first phase encoding gradient pulse which samples k-space along a first axis passing through the thin slab;
   c) producing a second phase encoding gradient pulse which samples k-space along a second axis oriented in the plane of the thin slab;
   d) acquiring an NMR signal in the presence of a readout gradient which samples k-space along a third axis oriented in the plane of the thin slab and perpendicular to the second axis;
   e) repeating steps a) through d) a plurality of times and changing the first phase encoding gradient pulse to sample k-space completely along said first axis;

f) repeating step e) a plurality of times and changing the second phase encoding gradient pulse to sample k-space at a corresponding plurality of locations distributed along said second axis;

g) incrementing the position of the thin slab in the three-dimensional volume of interest along said first axis and repeating step f) to sample k-space at other locations distributed along said second axis;

h) repeating step g) until k-space is completely sampled along said second axis; and i) reconstructing the image from the acquired NMR signals.

9. The method as recited in claim 1 in which step h) is performed a plurality of times to increment the position of the thin slab completely through said three-dimensional volume of interest along said first axis.

10. The method as recited in claim 1 in which the samples of k-space acquired in step f) along said second axis are interleaved with other of the samples of k-space acquired in step f) along said second axis when the thin slab position is incremented to a different position along said first axis.

11. The method as recited in claim 1 in which a navigator pulse sequence is performed at each location of the thin slab as it is incremented along said first axis to acquire said NMR signals, and a navigator NMR signal is acquired at each thin slab location and employed to correct the corresponding NMR signals acquired at that thin slab location.

* * * * *